United States Patent [19]

Hickner et al.

[11] 4,188,340
[45] Feb. 12, 1980

[54] POLYETHERS HAVING AMINOTHIOETHER SIDE CHAINS

[75] Inventors: Richard A. Hickner, Lake Jackson, Tex.; Hugh A. Farber, Midland, Mich.

[73] Assignee: The Dow Chemical Company, Midland, Mich.

[21] Appl. No.: 613,662

[22] Filed: Sep. 15, 1975

Related U.S. Application Data

[60] Continuation-in-part of Ser. No. 427,605, Dec. 26, 1973, abandoned, which is a division of Ser. No. 846,946, Aug. 1, 1969, Pat. No. 3,804,900.

[51] Int. Cl.$^2$ ............................................ C07C 93/06
[52] U.S. Cl. .......................... 260/567.6 P; 260/584 R; 260/570.5 S; 260/501.13; 260/501.15
[58] Field of Search ................................... 260/567.6 P Primary Examiner—James H. Reamer

[57] ABSTRACT

Polyethers having utility as flocculating aids and epoxy curing agents comprise repeating monomer units represented by the general formula:

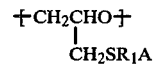

wherein $R_1$ is a divalent organic radical and A is an amine or an ammonium radical.

11 Claims, No Drawings

POLYETHERS HAVING AMINOTHIOETHER SIDE CHAINS

CROSS-REFERENCE TO RELATED APPLICATION

The present application is a continuation-in-part of my previous application, Ser. No. 427,605, filed Dec. 26, 1973, now abandoned, which was a division of Ser. No. 846,946, filed Aug. 1, 1969, now U.S. Pat. No. 3,804,900 issued Apr. 6, 1974.

BACKGROUND OF THE INVENTION

This invention relates to novel polyethers having aminothioether side chains and their utility as flocculating aids and epoxy curing agents.

It is well known to prepare polyethers by polymerizing an alkylene oxide (so-called epoxide) alone or with other alkylene oxides, usually in the presence of an active hydrogen activator such as an alcohol or a polyol. Such polymerizations are generally facilitated by using a Friedel-Crafts catalyst such as boron trifluoride and the like to yield polymers represented by the general formula:

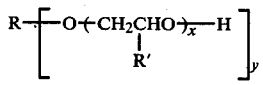

wherein R is hydrogen or the residue of an organic active hydrogen initiator and R' is hydrogen or alkyl and x and y are individually positive whole numbers.

It is also known to polymerize epihalohydrin alone or with other epihalohydrins or alkylene oxides, preferably in the presence of an active hydrogen initiator and/or a Friedel-Crafts catalyst, to yield polyethers in which at least a portion of the side chains are haloalkyl. As taught in U.S. Pat. Nos. 2,619,508 and 3,415,902, the halogen atoms of the side chains can be replaced with alkylthio radicals or hydroxyalkylthio radicals by reacting the polyether having haloalkyl side chains with alkali metal mercaptides or mercaptoalkanol dissolved in alkali.

Polyethers having aminothioether side chains have not been previously known.

SUMMARY OF THE INVENTION

In accordance with the present invention, polyethers having pendant aminothioether side chains, described hereinafter in more detail, are provided. These polyethers possess surprising properties making them useful as flocculating aids and epoxy curing agents.

Characteristically, these novel polyethers comprise at least 10 mole percent of repeating monomer units represented by the general formula:

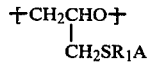

wherein $R_1$ is a divalent organic radical with each valence existing on a carbon atom and A is (1) an amine radical represented by the general formula: $-NR_2R_3$ or (2) an ammonium salt radical represented by the general formula:

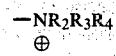

wherein $R_2$ and $R_3$ are individually hydrogen or a monovalent organic radical with the valence existing on a carbon atom, $R_2$ and $R_3$ are collectively a divalent organic radical having at least two carbon atoms with each valence existing on a different carbon atom, $R_4$ is hydrogen or a monovalent organic radical with the valence existing on a carbon atom and X is an anion of an ammonium salt.

In addition to their utility as flocculating aids and epoxy curing resins, these novel polyethers also are useful as paper pulp drainage aids.

DESCRIPTION OF THE PREFERRED EMBODIMENTS

The polyethers of the present invention have as an essential component a repeating monomer unit represented by the general formula:

$$\text{+CH}_2\text{CHO+} \atop \text{CH}_2\text{SR}_1\text{A}$$

wherein $R_1$ and A are as generally defined hereinbefore. For the essential component to impart the desired functions to the polyether, said component must comprise at least 10 mole percent of the polyether.

Illustratively, $R_1$ is a divalent organic radical such as alkylene and substituted alkylene; arylene and substituted arylene, arylenealkylene, e.g.,

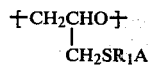

and substituted arylenealkylene; cycloalkylene and substituted cycloalkylene; alkylenethioalkylene, e.g., $-(CH_2)_3S(CH_2)_3-$, and substituted alkylenethioalkylene; poly(alkylenethio)alkylene, e.g., $-(CH_2CH_2S)_3(CH_2)_4-$, and substituted poly(alkylenethio)alkylene; e.g.,

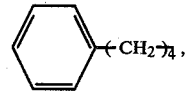

alkyleneoxyalkylene, e.g., $-(CH_2)_2O-(CH_2)_2-$, and poly(alkyleneoxy)alkylene, e.g.,

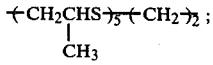

and the like wherein such divalent radicals have at least 2 carbon atoms and each valence exists on a different carbon atom. $R_1$ can also be iminomethylene, i.e.,

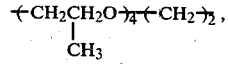

Of the above divalent radicals, $R_1$ is preferably alkylene having from 2 to 12 carbon atoms, hydroxyalkylene having from 2 to 12 carbon atoms wherein hydroxy is bonded to a carbon atom at least one carbon atom removed from S; alkylenethioalkylene and poly(alkylenethio)alkylene represented by the general formula: $+[(CH_2)_n S]_m (CH_2)+_o$ wherein n is an integer from 2 to 12, m is an integer from 1 to 5 and o is an integer from 1 to 4; and iminomethlene,

Specifically, A may be an amine radical, $-NR_2R_3$, or an ammonium salt radical,

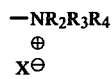

Illustratively, $R_2$ and $R_3$ are individually hydrogen or monovalent organic radical such as alkyl and substituted alkyl, including hydroxyalkyl, alkoxyalkyl and the like; aryl and substituted aryl including alkoxyaryl; aralkyl and substituted aralkyl; cycloalkyl and substituted cycloalkyl; alkyleneiminoalkylamine and poly(alkyleneimino)alkylamine, e.g.,

alkyleneoxyalkylamine and poly(alkyleneoxy)alkylamine; e.g., $-(CH_2CH_2O)_2CH_2CH_2N(CH_3)_2$; alkylenethioalkylamine and poly(alkylenethio)alkylamine, e.g.,

and the like. Also $R_2$ and $R_3$ collectively are a divalent organic radical having at least two carbon atoms with each valence existing on a different carbon atom, for example, alkylene, alkyleneoxyalkylene, alkylenethioalkylene, alkyleneiminoalkylene and the like. Usually such divalent groups have from 2 to 7 carbon atoms.

Preferably $R_2$ and $R_3$ are individually hydrogen, alkyl having from 1 to 12 carbon atoms, aryl having from 6 to 12 carbon atoms, hydroxyalkyl having from 2 to 12 carbon atoms, or poly(alkyleneimino)alkylamine represented by the general formula:

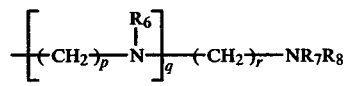

wherein $R_6$, $R_7$ and $R_8$ are individually hydrogen or a monovalent organic radical with the valence existing on a carbon atom; p is an integer from 2 to 8, and q is an integer from 1 to 5 and r is an integer from 2 to 8. Preferably $R_2$ and $R_3$ are collectively an alkylene radical having from 2 to 6 carbon atoms or a divalent organic radical represented by the general formula:

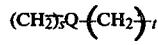

wherein Q is $-O-$, $-S-$, or

and s and t are individually an integer from 1 to 3 wherein the sum of s and t is 2, 3 or 4. $R_4$ is a monovalent radical such as hydrogen, alkyl and substituted alkyl, aryl and substituted aryl, aralkyl and substituted aralkyl, cycloalkyl and the like. Preferably $R_4$ is hydrogen or an alkyl radical having from 1 to 12 carbon atoms. X is any anion common to ammonium salts, such as halide, sulfate, nitrate, carboxylate and the like with the halides such as chloride or bromide being preferred.

These polyethers have molecular weights ranging from a few hundred up to about 3 million, with preferred polyethers ranging from 300 up to 2 million. Particularly effective epoxy curing agents of these polyethers are those having molecular weights ranging from about 300 to about 10,000.

In preferred embodiments the polyethers are more specifically represented by the general statistical formula:

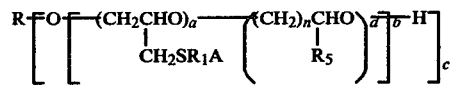

wherein R is hydrogen or the residue of an organic active hydrogen initiator; $R_5$ is hydrogen or a monovalent organic radicl with the valence existing on a carbon atom; a is a positive integer and d is O or a positive integer provided that the ratio of a to d is such that the polyether contains at least 10 mole percent of

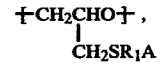

preferably ratio is from 1:20 to 1:0; b is a positive integer, preferably from 1 to 10,000, and c is a positive integer, preferably from 1 to 8, and n is a positive integer from 1 to 4.

Exemplary of $R_5$ are hydrogen and monovalent radicals such as alkyl and substituted alkyl, aryl and substituted aryl and the like. Preferably, alkyl has from 1 to 4 carbon atoms and aryl has 6 to 12 carbon atoms. Substituted alkyls include haloalkyl; mercaptoalkyl; alkoxyalkyl wherein alkoxy has from 1 to 20 carbon atoms, particularly alkoxymethyl; aryloxyalkyl wherein aryloxy has from 6 to 20 carbon atoms, particularly aryloxymethyl, alkylthioalkyl wherein alkylthio has 1 to 20 carbon atoms and the like. Substituted aryls include haloaryl, mercaptoaryl, alkoxyaryl, aryloxyaryl and the like.

It is further understood that $R_5$ may be different radicals within a single polyether molecule. For example, the polyether may have the statistical formula:

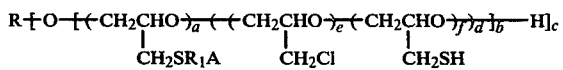

wherein e and f are positive integers.

In general the polyethers of the present invention can be prepared by first polymerizing an epihalohydrin or copolymerizing the epihalohydrin with one or more alkylene oxides and subsequently substituting at least a portion of halogen atoms on the polyether side chains with aminoalkylenemercaptide.

Epihalohydrins used in the polymerization step include epichlorohydrin and epibromohydrin.

Examples of suitable alkylene oxides for use in copolymerization with epihalohydrin are the following: alkylene oxides, such as ethylene oxide, propylene oxide, 1,2-butylene oxide, 2,3-butylene oxide, isobutylene oxide and octylene oxide; glycidol; glycidyl ethers or thioethers, such as methyl glycidyl ether, allyl glycidyl ether, phenyl glycidyl ether, butylglycidyl ether, octylglycidylthioether and p-dodecylphenyl glycidyl ether; and others such as tetrahydrofuran and trimethylene oxide.

In the copolymerization of epihalohydrin with one or more alkylene oxides, the addition of epihalohydrin and alkylene oxide during copolymerization may be alternated to yield polyethers having haloalkyl side chains in predetermined structural patterns. For example, if one mole of epichlorohydrin and one mole of ethylene oxide are added to 0.1 mole of ethyl alcohol as the active hydrogen initiator, the predominant product obtained would have the statistical formula:

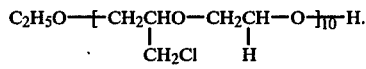

Alternatively, if two moles of epichlorohydrin are added to 0.1 mole of ethyl alcohol followed by the addition of 5 moles of ethylene oxide, a species having the following statistical formula would be obtained:

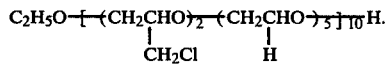

Generally speaking, the variation in spacing between the side chains containing halogen atoms along the polyether chain is unlimited, thus it is possible to control the number of the aminothioether side chains in the final product. In addition, the active hydrogen initiator may contain one or more halogens, such as ethylene chlorohydrin or glycerin dihalide, which halogens would represent reactive sites for the replacement reactions.

In carrying out polymerization or copolymerization to prepare polyethers containing halomethyl side chains as described above, cyclic ether monomer or mixtures of cyclic ether monomers, the active hydrogen initiator and a Friedel-Crafts catalyst are preferably charged into a closed vessel and heated until polymerization is complete. In the case where a copolymer is being formed, the monomers, a prepolymer or mixture thereof may be charged simultaneously or consecutively or alternatively one or the other in whatever mole ratios are needed to form the desired product. The proportion of catalyst may vary from 0.05 to 15 weight percent of the reacting materials, e.g., monomers, prepolymers, or mixtures thereof, with 0.2 to 5 weight percent being preferred. The reaction mass is advantageously agitated during polymerization which is generally carried out at temperatures within the range of 0° to 200° C., preferably from 20° to 100° C. Alternatively, polymerization may be carried out with monomeric and/or polymeric reactants, catalyst and polymer product all dissolved or suspended in an organic diluent. In such instances, equal proportions of diluent are used, with suitable diluents including diethyl ether, dioxane, diisopropyl ether, petroleum ether, benzene and n-hexane. It is advantageous to choose a diluent which boils at about polymerization temperature, and to heat the mass to induce gentle reflux, thereby assisting in the close control of the reaction temperature. Other polymerization methods which are well known in the art may also be suitably employed. For example, high molecular weight polyethers can be prepared by contacting cyclic ether monomer with a Friedel-Crafts catalyst.

Examples of suitable active hydrogen initiators include water and organic active hydrogen initiators such as aliphatic monohydric alcohols, e.g., methanol, ethanol, 2-butanol and 1-octanol; alcohol ethers, such as ethylene glycol monomethyl ether and ethylene glycol monoehtyl ether; aliphatic polyhydric alcohols, e.g., ethylene glycol, propylene glycol, 1,3-butanediol, 1,4-butanediol, glycerol and sorbitol; hydroxyl terminated polyethers, e.g., polyethylene glycols, polypropylene glycols, polybutylene glycols and dihydroxypropyl ether of bisphenol A; haloalcohols, e.g., ethylene chlorohydrin and glycerol dichloride; monohydric phenols, e.g., phenol, xylenol and p-chlorophenol; dihydric mononuclear phenols, e.g., resorcinol and hydroquinone; polyhydric mononuclear phenols, e.g., phloroglucinol; dihydric dinuclear phenols, e.g., bisphenol A and bis-p-hydroxyphenyl methane; polyhydric polynuclear phenols, e.g., phenolic novolacs made by condensation of phenol with formaldehyde under acid conditions; sugars, e.g., sucrose, glucose, fructose, maltose and other mono-, di- and polysaccharides; and other active hydrogen compounds, e.g., thiols, amines and the like.

Examples of catalysts suitable for the polymerization reaction include the Friedel-Crafts catalysts such as the Lewis acids and organometallic products exhibiting the reactivity of Lewis acids, such as $BF_3$, $AlCl_3$, $SnCl_4$, $ZnCl_2$, $FeCl_2$, $FeCl_3$, $FeBr_2$, $FeBr_3$, $BeCl_2$, $BCl_3$, $SbCl_5$, $TiCl_4$, $CoCl_2$, $NiCl_2$, $BiCl_2$, $InCl_3$, $ZrCl_4$, titanium tetraalkyl esters, aluminum alkyls and aluminum alkoxides, diethyl zinc in combination with alumina, or oxygen, HF and complexes of HF with $PF_5$, protonic acids and acid salts such as sulfuric acid, phosphorous acid, phosphoric acid, sodium hydrogen sulfate and the like, and combinations thereof.

The crude polyether product resulting from the polymerization process, in addition to containing the desired epihalohydrin polymer, may contain unreacted monomer. The monomer can be removed by warming the crude product and subjecting it to reduced pressure.

The epihalohydrin polymer is readily converted to polyether having pendant aminothioether side chains, as described hereinbefore, by one of several techniques.

In accordance with one technique, a mercaptoamine or a mercaptoamine hydrohalide is mixed with the epihalohydrin polymer and a base such as an alkali metal hydroxide, preferably by dissolving the components in an inert diluent such as a lower alkyl alcohol, e.g., methanol, ehtanol, or isopropanol, in which the alkali metal halide salt which forms is poorly soluble. The reaction mixture is heated at 25° to 150° C., preferably 40° to 90° C. The time required depends on the charge. Other inert diluents include dioxane, tetrahydrofuran, glycols, glycol ethers, N-methyl pyrrolidone, and the like. It is understood that if the epihalohydrin polymer is a liquid, the use of solvents can be dispensed with and the polymer can be dissolved in the desired amount of the mercaptoamine. If the epihalohydrin polymer is solid, it can be dissolved in the aforementioned diluents or in an excess of the mercaptoamine.

Bases which can be suitably employed are the alkali metals, alkali metal alcoholates, alkali metal hydroxides, alkali metal carbonates, quaternary ammonium compounds such as tetramethyl ammonium hydroxide, and tertiary amines such as pyridine, quinaldine, quinuclidine and triethylamine.

The ratio of mercaptoamine to equivalents of halogen in the epihalohydrin polymer is not critical and can be amounts equivalent to the amount of halogen to be replaced or can be amounts in substantial excess so as to serve as a solvent or diluent. Usually the ratio of mercaptoamine to equivalents of halogen ranges from about 0.05 to about 10 times the equivalent weight of halogen, preferably from about 1 to 2 times. The amount of alkali metal hydroxide used is ordinarily that required on an equivalent basis equal to the amount of halogen to be replaced or in excess of that amount, preferably the alkali metal hydroxide and the mercaptoamine employed are the stoichiometric quantities required to replace the desired amount of halogen. The amount of halogen replaced is at least the amount necessary to yield a polyether in which at least 10 mole percent comprises

preferably from about 12 to about 100 mole percent.

In accordance with a second and similar technique for coverting the haloalkyl side chain to aminothioether side chains, the mercaptoamine is first reacted with an akali metal or alkaline metal hydroxide to form a metal aminomercaptide. The metal aminomercaptide is then reacted with the epihalohydrin polymer, preferably in an inert diluent as described above, to form the desired polyether.

Mercaptoamines which are employed in the above techniques are represented by the general formula: $HSR_1A$ wherein $R_1$ and A are as defined hereinbefore. Illustratively, such mercaptoamines include N-(mercaptoalkyl)amines, e.g., N-(2-mercaptoethyl)amine, N-(2-mercaptoethyl)dimethylamine, N-(2-mercapto-1-methylethyl)diethylamine, N-(3-mercaptopropyl)ethylamine, N-(3-mercapto-2-methylpropyl)amine, N-(3-mercaptooctyl)amine, N-(4-mercaptodecyl)amine, N-(4-mercaptobutyl)diethanolamine, and the like; N-(mercaptohydroxyalkyl)amines wherein hydroxy is at least one carbon removed from mercapto, e.g., N-(3-mercapto-2-hydroxypropyl)dimethylamine, N-(4-mercapto-2-hydroxybutyl)amine, and the like; N-(mercaptocycloalkyl)amines, e.g., N-(4-mercaptocyclohexyl)amine, N-(3-mercaptocyclopentyl)ethanolamine, N-(4-mercapto-2-hydroxycycloheptyl)amine, and the like; N-(mercaptoaryl)amines, e.g., N-(2-mercaptophenyl)diethylamine, N-(4-mercaptophenyl)amine, N-(4-mercapto-2-hydroxyphenyl)amine, and the like; N-(mercaptoaralkyl)amines, e.g., N-(4-mercaptobenzyl)amine, N-(3-mercapto-2-phenylpropyl)amine, and the like; and other mercaptoamines such as N-(2-mercaptoethyl)morpholine, N-(2-mercaptoethyl)ethyleneamine and the like. Other suitable mercaptoamines include the (mercaptoalkylthioalkyl)amines and [mercaptopoly(alkylenethio)alkyl]amines, e.g.,

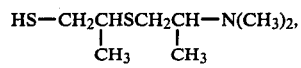

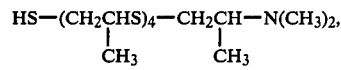

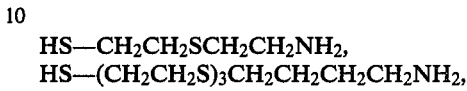

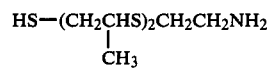

and the like; (mercaptoalkyliminoalkyl)amines and [mercaptopoly(alkyleneimino)alkyl]amines. e.g., $HSCH_2CH_2NHCH_2CH_2NH_2$, $HS$-$(CH_2CH_2NH)_3CH_2CH_2NH_2$,

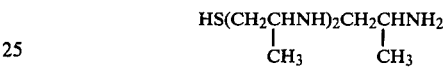

and the like; and (mercaptoalkoxyalkyl)amines and [mercaptopoly(alkyleneoxy)alkyl]amines, e.g., $HSCH_2CH_2OCH_2CH_2NH_2$, $HS$-$(CH_2CH_2O)_3CH_2CH_2NH_2$ and the like. In addition, thiourea, $S=C(NH_2)_2$, or similar such compounds may be employed in place of mercaptoamine to yield an aminothioether side chain having the structural formula:

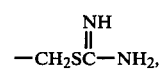

or in the ammonium salt form, e.g.,

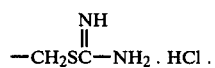

It is further understood that suitable mercaptoamines may be employed in their ammonium salt forms. Mercaptoamines described above are generally known and can be prepared by conventional methods. AS an illustration, however, N-(2-mercaptoethyl)amine and substituted N-(2-mercaptoethyl)amines are easily prepared by reacting ethylenimine

or substituted ethylenimine

[R''=alkyl, aryl, hydroxyalkyl, etc.] with hydrogen sulfide. Alternatively, the mercaptoamines may be prepared by displacing halogen from a halomercaptan having the desired structure with an amine.

In another technique the haloalkyl side chains of the epihalohydrin polymer is converted to aminothioether side chains by first replacing the halogen atoms with —SH and subsequently reacting the resulting mercapto containing polymer having the formula:

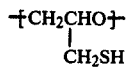

with a haloamine, preferably in the presence of strong base such as sodium hydroxide, or by reacting the mercapto containing polymer with ethylenimine or substituted ethylenimine. Other techniques which are equally apparent to those skilled in the art may also be used to prepare the polyether of the present invention. It is understood that the particular technique of preparation is not critical and that the resulting polyether having aminothioether side chains is the primary teaching of the present invention.

Wet solutions or dispersions of polyethers having pendant aminothioether side chains are good flocculating aids for starch dispersions, clay dispersions, sewage and the like. However, it is generally found that such polyethers tend to lose some of their flocculating activity when dried. The resulting polyethers, particularly those having aminothioether side chains in which nitrogen is bonded to a hydrogen, are very useful epoxy curing agents, especially polyethers having molecular weights ranging from about 300 to about 10,000. In addition, the polyethers of this invention are excellent paper pulp drainage aids.

Such polyethers are, in general, viscous liquids to moderately low melting solids which, in the free amine form, are insoluble in water and soluble in dilute aqueous acid. Such polyethers are readily soluble in many organic solvents such as lower alkyl alcohols such as methanol, ketones, such as acetone and chlorinated hydrocarbons such as methylene chloride. The polyethers in the ammonium salt form are soluble in water and are not as soluble in the organic solvents.

The following examples are given to further illustrate the invention and should not be construed as limiting its scope. In the following examples, all parts and percentages are by weight unless otherwise indicated.

In the following examples, the following test methods are used to determine the flocculating properties of the polyethers having aminothioether side chains.

Starch Flocculation Test—A 5.0 gram portion of arrow root starch is dispersed in 100 ml of distilled water in a 100 ml graduated cylinder. A 1-ml portion of 0.05% solution of polyether product is added to the starch dispersion in three 0.33 ml increments, the dispersion being shaken after the addition of each increment. The rate of fall of the interface from the 90 ml mark to the 50 ml mark of the graduated cylinder is recorded. Controls in which no polyether product or other flocculating agent has been added generally have a rate of fall of about 0.4 in/min.

Pulp Drainage Test—TAPPI Test Method—TAPPI T-227.

Sewage Flocculation Test—A 1- to 8-ml portion of a 0.1% solution of polyether product is dispersed in one liter of common sewage water in a one liter vessel. The sewage water is then stirred at 100 rpm for 5 minutes followed by stirring at 30 rpm for 5 minutes. The sewage water is then allowed to settle for 5 minutes after whih a sample is removed from vessel at one inch below the surface of the sewage water. The sample is then analyzed for suspended solids in parts per million. The results are given in percent of total solids removed.

EXAMPLE 1

A solution of 40 g (1.0 mole) of NaOH in 50 ml of water is slowly added to a suspension of 84.8 g (0.5 mole) of N-(2-mercaptoethyl)amino-hydrochloride, HSCH$_2$CH$_2$NH$_2$.HCl, in 250 ml of isopropyl alcohol. The resulting mixture is heated to 80° C. and 46.3 g (0.5 equivalent of Cl) of propylene glycol-initiated polyepichlorohydrin (Mol. Wt. ~450) is added dropwise to the heated mixture. The reaction mixture is heated at reflux for six hours and then filtered to remove salt precipitate. The filtrate is distilled at reduced pressure to remove water and isopropyl alcohol, and the residue is redissolved in fresh isopropyl alcohol and refiltered. The isopropylalcohol is removed and the remaining polyether product retained. The polyether product is found to have the following structure:

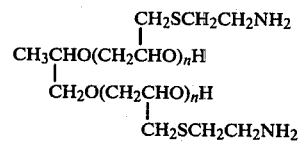

wherein n=2 or 3. The polyether is insoluble in water at 2.5 percent of polyether in water, but is readily dissolved in HCl. The polyether product is mixed with a liquid polypropylene-oxide epoxy resin. The mixture is applied to a substrate in the form of a thin film and allowed to cure overnight. The resulting film exhibits the characteristics of cured polypropyleneoxide epoxy resin.

EXAMPLE 2

An 8.8-g portion (0.22 mole) of NaOH and 11.35 g (0.10 mole) of N-(2-mercaptoethyl)amine hydrochloride are mixed together with 40 ml of isopropylalcohol and the mixture is heated to a temperature of 38° C. A solution of 91.8 g (0.10 equivalent of Cl) of high molecular weight propylene oxide/epichlorohydrin copolymer (90/10) (iron catalyzed) in 284 g of dioxane is added to the mixture over a two hour period while maintaining the temperature of the reaction mixture below 43° C. The reaction mixture is heated slowly to 70° C. and allowed to cool. The cooled mixture is filtered to remove salt and the filtrate is evaporated to a brown viscous polymer having the statistical formula:

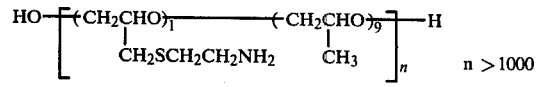

The polyether product in dioxane is added to a starch suspension such that the resulting concentration of polyether is about 10 ppm. The rate of fall of starch-water interface is substantially increased.

EXAMPLE 3

A 22.7-g portion (0.2 mole) of N-(2-mercaptoethyl)amine hydrochloride and 17.6 g (0.44 mole) of NaOH are mixed together in 300 ml of isopropyl alcohol and the initial exothermic temperature of 40° C. is cooled to 25° C. An 18.6-g portion (0.2 equivalent of Cl) of propylene glycol initiated polyepichlorohydrin (Mol. Wt. ~1150) is added to the cooled mixture over a 15 minute period, stirred at 25° C. for 2 hours, heated to 40° C. for 2 hours and then to 55° C. for 2 hours. The reaction mixture is allowed to stand overnight at 25° C., filtered to remove precipitated salt, and evaporated to remove isopropanol. The result polyether represented by the chemical formula:

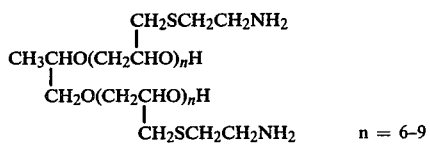

is insoluble in water at 2.5 percent of polyether in water and is moderately soluble in 0.1 N $H_2SO_4$.

EXAMPLE 4

A 27.4-part portion of N-[2-(2-mercaptoethylthio)ethyl]amine [$HSCH_2CH_2SCH_2CH_2NH_2$], 17.6 parts of NaOH and 300 ml of isopropanol are mixed in a reaction vessel and the reaction mixture is cooled to 25° C. An 18.6-part portion of polyepichlorohydrin (Mol Wt=450) is added to the cooled mixture over a 15 minute period, stirred at 25° C. for 2 hours, heated to 40° C. for 2 hours and finally heated to 55° C. for 2 hours. The reaction mixture is allowed to stand overnight at 25° C., and is filtered to remove precipitated NaCl. The resulting polyether product has repeating units having the structural formula:

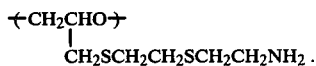

EXAMPLE 5

A 24-part portion of N-[2-(2-mercaptoethylimino) ethyl]amine $$[HSCH_2CH_2\overset{H}{N}CH_2CH_2NH_2],$$

17.6 parts of NaOH and 300 ml of isopropanol are mixed in a reaction vessel and the reaction is cooled to 25° C. An 18.6-part portion of polyepichlorohydrin (Mol Wt=450) is added to the cooled mixture over a 15 minute period, stirred at 25° C. for 2 hours, heated to 40° C. for 2 hours and finally heated to 55° C. for 2 hours. The reaction mixture is allowed to stand overnight at 25° C. and is filtered to remove precipitated NaCl. The resulting polyether product has repeating units having the structural formula:

EXAMPLE 6

A 28.5-gram portion of an epichlorohydrin/ethylene oxide copolymer (12/88) having a molecular weight of 1 million is dissolved in 400 ml of dioxane at 80° C. with stirring. An 80-gram portion of 50% aqueous sodium hydroxide and 57 grams of N-(2-mercaptoethyl)amine hydrochloride in 100 ml of water are added to the solution at 70° C. The reaction mixture is digested at 70° C. for 12 hours. The resulting polyether is isolated and found to have the following statistical formula:

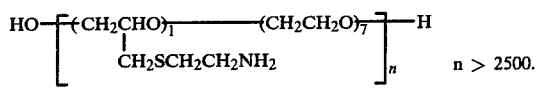

A portion of the reaction mixture is tested for flocculating activity using the hereinbefore described starch flocculation test and the rate of fall of the interface is found to be 4 inches/minute.

In the manner described above N-(2-mercaptoethyl)amine hydrochloride is reacted with epichlorohydrin/ethylene oxide copolymer (50/50) having a molecular weight greater than 1 million. The resulting polyether exhibits flocculating activity in starch similar to that of the above polyether.

EXAMPLE 7

The polyether product of Example 6 is prepared by a second technique wherein the epichlorohydrin/ethylene oxide copolymet (12/88) in dioxane is reacted with NaSH and subsequently reacted with ethylenimine.

EXAMPLE 8

The polyether product of Example 6 is tested as a paper pulp drainage aid according to TAPPI T-227 wherein 0.25 percent of polyether based on total solids is dispersed in a liter of an aqueous suspension of paper pulp. At pH of 7.5 the drainage rate is 430 ml of overflow for the suspension containing the polyether whereas in a control sample containing no polyether the drainage rate is 125 ml of overflow.

EXAMPLE 9

A similar polyether is prepared by reacting the epichlorohydrin/ethylene oxide copolymer of Example 6 with NaSH and reacting the resulting copolymer product with 3-chloro-2-hydroxypropyl trimethylammonium chloride in the presence of sodium hydroxide to yield a cationic polymer having the statistical formula:

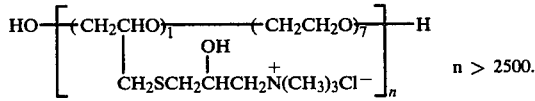

The polymer exhibits good activity as a starch flocculant and is a good paper pulp drainage aid.

EXAMPLE 10

The epichlorohydrin/ethylene oxide copolymer of Example 6 is reacted in dioxane with thiourea [$S=C(NH_2)_2$] to yield a polyether having the following statistical formula:

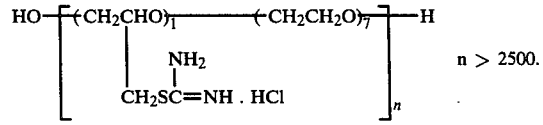

The resulting chalky-white solution is dissolved in water to give a turbid liquid having a pH of 6. The turbid liquid exhibits good activity as a starch flocculant.

EXAMPLE 11

An epichlorohydrin/ethylene oxide copolymer (50/50) is reacted with sufficient NaSH in isopropyl alcohol to yield a polyether in which essentially all of the chlorine atoms are replaced with —SH. A 200-part portion of the resulting polyether having mercaptan side chains (0.76 equiv.) is dissolved in 500 parts of methanol. The solution is charged to a 1 liter flask and allowed to stand overnight. A 9.8 part portion of ethylenimine (0.228 equiv.) is added dropwise to the solution over a 15 minute period. The reaction mixture is heated at 60° C. for 2 hours and the resulting polyether is isolated by evaporation of solvent. Analytical analysis for nitrogen indicates a 92% yield of a polyether having repeating ether units of the statistical proportions:

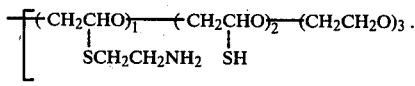

EXAMPLE 12

A polyepichlorohydrin is prepared by reacting a polypropylene glycol (Mol Wt=200) with four moles of epichlorohydrin. One chlorine equivalent of the resultant polyepichlorohydrin is dissolved in 200 ml of methanol and reacted with 1.5 equivalents of NaSH to yield a polyether having a plurality of pendant thiol side chains. The resultant polyether is then charged to a 500 ml threenecked flask and 105 g of a mixture containing 60% N-aminoethylaziridine, 35% N-[(2-aminoethyl-)aminoethyl]aziridine and 5% N-[(2-aminoethyl)aminoethyl]aminoethylaziridine is added dropwise to the polyether. The reaction temperatures rises to 50° C. and is maintained at 50°-60° C. for an additional 5 hours to yield a moderately viscous amine. A solution of 5.8 g of the above amine and 18.7 g of diglycidyl ether of bisphenol A is prepared and a 2 mil film is cast on a tin plate. Upon allowing the film to stand overnight at room temperature, the film cures to a tough film free from blushing.

EXAMPLE 13

A 45-g portion of epihalohydrin/ethylene oxide copolymer (50/50) (Mol Wt>million) is dissolved in 405 g of ethanol by heating at 55° C. under nitrogen. A solution of 21.20 g of N-(2-mercaptoethyl)amine and 13.65 g of anhydrous potassium hydroxide in 150 g of ethanol is added to the above solution. The reaction mixture is heated at reflux for 4¾ hours.

A solution of the polyether product represented by the statistical formula,

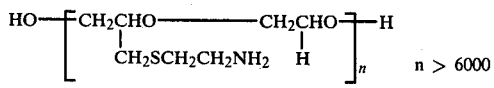

is recovered. Upon carrying out the starch flocculation test using the polyether product, the interface rate of fall of 13.8 in/min is observed. Upon carrying out the sewage flocculation test using a 4 ml portion of a 0.1% solution of polyether product, approximately 74.7 percent of total solids are removed. When the sewage flocculation test is carried out on a control sample in which no flocculant is added, approximately 38.0 percent of total solids are removed. When the same concentration of a commercial flocculant, sodium polystyrene sulfonate is employed in the same test procedure, approximately 59.5 percent of total solids are removed.

What is claimed is:

1. A polyether represented by the general statistical formula:

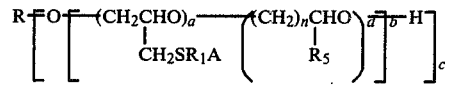

wherein R is hydrogen or the residue of an active hydrogen initiator selected from the group consisting of monohydric alkyl alcohols, polyhydric alkyl alcohols, hydroxyl terminated polyalkylene polyethers and haloalkyl alcohols; $R_1$ is alkylene, cycloalkylene, hydroxyalkylene, having 2 to 12 carbon atoms wherein the hydroxy group is bonded to a carbon at least one carbon removed from S, alkylenethioalkylene, poly(alkylenethio)alkylene, alkyleneoxyalkylene, poly(alkyleneoxy)alkylene, arylene or arylenealkylene wherein $R_1$ has at least 2 carbons and each of 2 valences exist on a different carbon; A is an ammonium salt radical represented by the general formula:

$$—N^{\oplus}R_2R_3R_4\,^{\ominus}X$$

wherein $R_2$ and $R_3$ are individually hydrogen, alkyl or hydroxyalkyl, $R_4$ is hydrogen or alkyl and X is an anion of an ammonium salt group; $R_5$ is hydrogen or alkyl; a is a positive integer and d is 0 or a positive integer provided that the ratio of a to d is such that the polyether contains at least 10 mole percent of

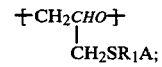

b is a positive integer; c is a positive integer; and n is a positive integer from 1 to 4.

2. The polyether according to claim 1 wherein $R_1$ is an alkylene radical having from 2 to 12 carbon atoms.

3. The polyether according to claim 1 wherein $R_1$ is an arylene radical having from 6 to 20 carbon atoms.

4. The polyether according to claim 1 wherein at least one of $R_2$ and $R_3$ is alkyl having from 1 to 12 carbon atoms or hydroxy alkyl having from 2 to 12 carbon atoms.

5. The polyether according to claim 1 wherein $R_2$ and $R_3$ are individually alkyl or hydroxyalkyl, $R_4$ is alkyl and $R_5$ is hydrogen or alkyl and X is a halide ion.

6. The polyether according to claim 1 wherein $R_4$ is an alkyl radical having from 1 to 12 carbon atoms.

7. The polyether according to claim 1 wherein X is halide, sulfate, nitrate or carboxylate.

8. The polyether according to claim 1 wherein $R_5$ is a haloalkyl radical having 1 carbon atom.

9. The polyether according to claim 1 wherein $R_5$ is an alkoxymethyl radical in which alkoxy has from 1 to 20 carbon atoms.

10. The polyether according to claim 1 wherein $R_5$ is an aryloxy radical in which aryloxy has from 6 to 20 carbon atoms.

11. The polyether of claim 1 represented by the formula:
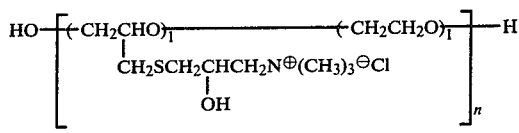
wherein n>2500.